United States Patent [19]
Roth et al.

[11] Patent Number: 5,665,063
[45] Date of Patent: Sep. 9, 1997

[54] METHODS FOR APPLICATION OF INTRALUMINAL PHOTOPOLYMERIZED GELS

[75] Inventors: Laurence A. Roth, Windham, N.H.; Stephen J. Herman, Andover, Mass.; Farhad Khosravi, Newton, Mass.; David Melanson, Chelmsford, Mass.; Michael Dumont, Stratham, N.H.

[73] Assignee: Focal, Inc., Lexington, Mass.

[21] Appl. No.: 265,448

[22] Filed: Jun. 24, 1994

[51] Int. Cl.$^6$ ................................................ A61M 25/00
[52] U.S. Cl. ................. 604/53; 604/96; 604/101; 604/21; 604/194; 604/195; 623/12
[58] Field of Search ............................. 604/19, 20, 21, 604/265, 96, 101, 49, 52, 53; 606/191–195

[56] References Cited

U.S. PATENT DOCUMENTS

| | | |
|---|---|---|
| 3,707,146 | 12/1972 | Cook et al. . |
| 3,987,000 | 10/1976 | Gleichenhagen et al. . |
| 4,023,559 | 5/1977 | Gaskell . |
| 4,080,969 | 3/1978 | Casey et al. . |
| 4,118,470 | 10/1978 | Casey et al. . |
| 4,190,720 | 2/1980 | Shalaby . |
| 4,233,493 | 11/1980 | Nath . |
| 4,248,214 | 2/1981 | Hannah et al. . |
| 4,336,809 | 6/1982 | Clark . |
| 4,385,344 | 5/1983 | Gonser . |
| 4,423,725 | 1/1984 | Baran et al. . |
| 4,443,430 | 4/1984 | Mattei et al. . |
| 4,445,892 | 5/1984 | Hussein et al. . |
| 4,451,568 | 5/1984 | Schneider et al. ........................ 623/1 |
| 4,496,345 | 1/1985 | Hasson . |
| 4,573,966 | 3/1986 | Weikl et al. . |
| 4,575,181 | 3/1986 | Ishikawa . |
| 4,578,061 | 3/1986 | Lemelson . |
| 4,588,395 | 5/1986 | Lemelson . |
| 4,669,465 | 6/1987 | Moore et al. . |
| 4,744,366 | 5/1988 | Jang . |
| 4,763,653 | 8/1988 | Rockey . |
| 4,799,479 | 1/1989 | Spears . |
| 4,824,436 | 4/1989 | Wolinsky . |
| 4,832,688 | 5/1989 | Sagae et al. . |
| 4,846,165 | 7/1989 | Hare et al. . |
| 4,846,174 | 7/1989 | Willard et al. . |
| 4,878,492 | 11/1989 | Sinofsky et al. . |
| 4,900,303 | 2/1990 | Lemelson . |
| 4,911,163 | 3/1990 | Fina ........................................ 606/192 |
| 4,938,763 | 7/1990 | Dunn et al. . |
| 4,969,912 | 11/1990 | Kelman et al. . |
| 5,080,893 | 1/1992 | Goldberg et al. . |
| 5,092,841 | 3/1992 | Spears . |
| 5,100,429 | 3/1992 | Sinofsky et al. . |
| 5,147,203 | 9/1992 | Seidenberg . |
| 5,156,613 | 10/1992 | Sawyer . |
| 5,169,395 | 12/1992 | Narciso, Jr. . |

(List continued on next page.)

FOREIGN PATENT DOCUMENTS

| | | |
|---|---|---|
| 0355200 | 2/1990 | European Pat. Off. . |
| 0402467 | 12/1990 | European Pat. Off. . |
| WO88/03389 | 5/1988 | WIPO . |
| WO89/12478 | 12/1989 | WIPO . |
| WO90/01969 | 3/1990 | WIPO . |
| WO91/12846 | 9/1991 | WIPO . |
| WO91/17731 | 11/1991 | WIPO . |
| WO92/21354 | 12/1992 | WIPO . |
| WO93/16687 | 9/1993 | WIPO . |
| WO93/17669 | 9/1993 | WIPO . |

(List continued on next page.)

*Primary Examiner*—Michael Powell Buiz
*Assistant Examiner*—Chalin Smith
*Attorney, Agent, or Firm*—Wolf, Greenfield & Sacks, P.C.

[57] ABSTRACT

Devices for providing polymeric layers on the interior surface of body lumens and spaces are disclosed. The devices can include proximal and distal occlusion elements to define the treatment space and an optical emitter to provide light for a photopolymerization procedure. The devices may include a molding member for providing a thick polymeric gel. Alternatively, devices without a molding member may be used to carry out an interfacial polymerization procedure.

37 Claims, 11 Drawing Sheets

U.S. PATENT DOCUMENTS

| | | | |
|---|---|---|---|
| 5,176,638 | 1/1993 | Don Michael | 604/101 |
| 5,196,005 | 3/1993 | Doiron et al. | |
| 5,199,951 | 4/1993 | Spears | 604/96 |
| 5,207,670 | 5/1993 | Sinofsky | |
| 5,209,748 | 5/1993 | Daikuzono | |
| 5,213,580 | 5/1993 | Slepian | |
| 5,232,444 | 8/1993 | Just et al. | |
| 5,250,070 | 10/1993 | Parodi | |
| 5,257,970 | 11/1993 | Dougherty | 604/20 |
| 5,279,546 | 1/1994 | Mische et al. | |
| 5,292,362 | 3/1994 | Bass et al. | |
| 5,298,018 | 3/1994 | Narciso | 604/21 |
| 5,306,249 | 4/1994 | Don Michel | |
| 5,312,333 | 5/1994 | Churinetz et al. | |
| 5,324,519 | 6/1994 | Dunn et al. | |
| 5,328,471 | 7/1994 | Slepian | |
| 5,372,585 | 12/1994 | Tiefenbrun et al. | |
| 5,397,307 | 3/1995 | Goodin | |
| 5,410,016 | 4/1995 | Hubbell et al. | |
| 5,425,723 | 6/1995 | Wang | |
| 5,454,794 | 10/1995 | Narciso et al. | |
| 5,460,610 | 10/1995 | Don Michael | |
| 5,462,529 | 10/1995 | Simpson et al. | |

FOREIGN PATENT DOCUMENTS

| | | |
|---|---|---|
| WO94/05342 | 3/1994 | WIPO |
| WO95/08289 | 3/1995 | WIPO |
| WO95/09024 | 4/1995 | WIPO |
| WO96/00102 | 1/1996 | WIPO |

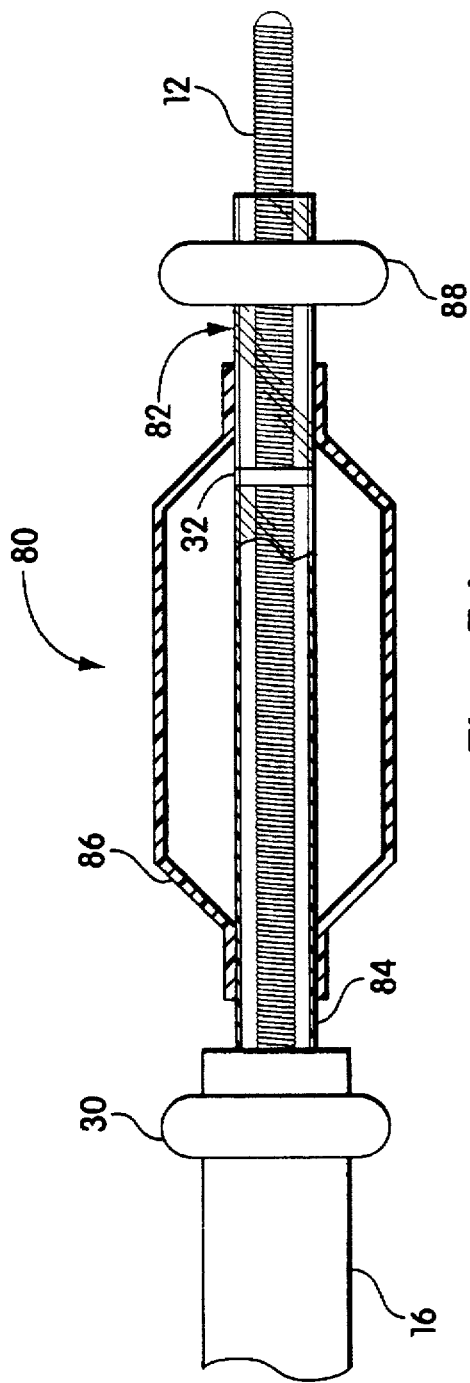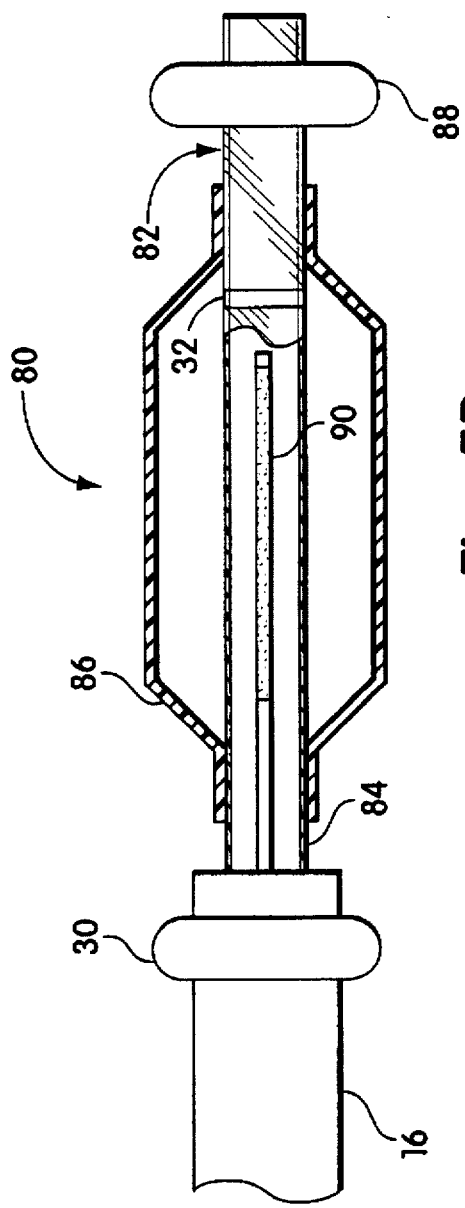
Fig. 5A
Fig. 5B

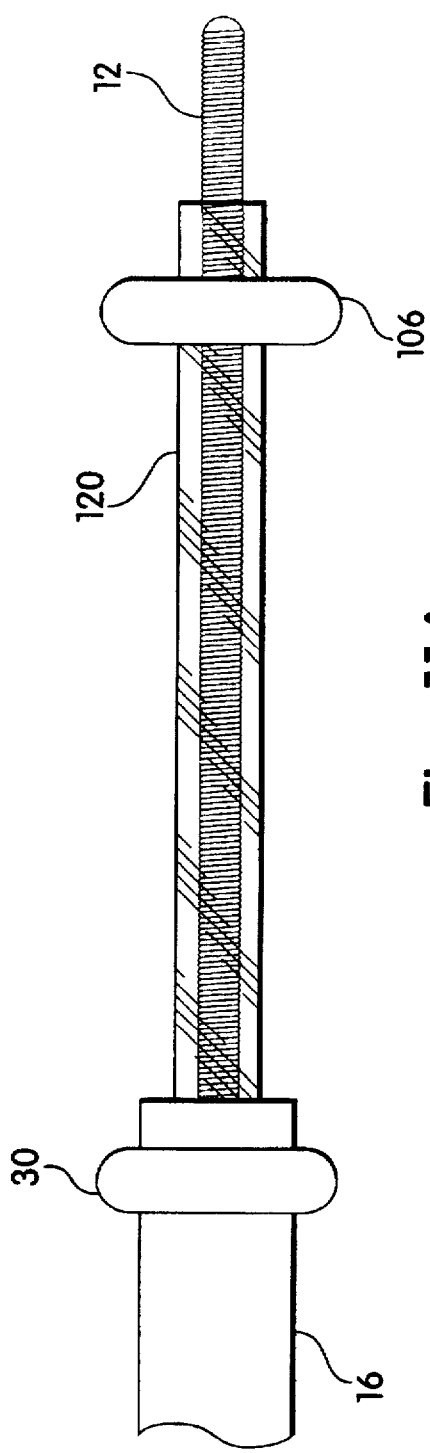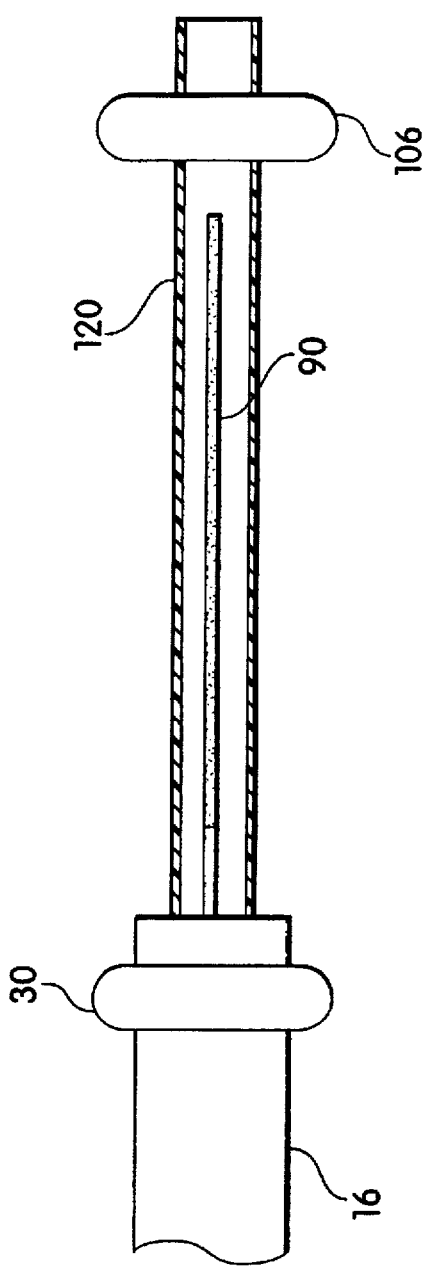

METHODS FOR APPLICATION OF INTRALUMINAL PHOTOPOLYMERIZED GELS

FIELD OF THE INVENTION

This invention relates to devices and methods for applying photopolymerizable gels to tissue lumens.

BACKGROUND OF THE INVENTION

U.S. Pat. No. 5,213,580, issued May 25, 1993 to Slepian et al., and International Patent Application No. PCT/US89/03593 by Slepian et al., published Mar. 8, 1990 as Publication Number WO 90/01969, both describe a system of endoluminal sealing in which a biodgradable polymer is introduced into the lumen of a blood vessel, positioned at a point of stenosis, and thermally reconfigured to seal and pave the interior of the vessel. International Patent Application No. PCT/US91/01242 by Slepian, published Sep. 5, 1991 as Publication Number WO 91/12846, describes a method for treatment of tubular organs in which a therapeutic agent is introduced into a region of a tissue lumen defined by two expansile members and allowed there to remain for a therapeutically effective period of time.

U.S. Pat. No. 5,410,016, issued Apr. 25, 1995 (Hubbell et al.) and U.S. patent application Ser. No. 08/024,657 (Hubbell et al.) both filed Mar. 1, 1993 disclose a number of photopolymerizable polymers that may be applied to living mammalian tissue, including living soft tissue in order to treat various medical conditions. For example, the polymers may be applied for the prevention of post-operative adhesions, protection of tissue surfaces, the local application of biologically active species, and the controlled release of biologically active agents to achieve local and systemic effects. The materials and conditions of application are selected to enhance desirable properties such as good tissue adherence without adverse tissue reaction, non-toxicity, good biocompatibility, biodegradability, and ease of application or handling.

The compositions that form the polymers generally include a light sensitive polymerization initiator applied as a coating to the tissue surface in a fluent form, such as a liquid. The coated tissue then is exposed to light to polymerize the composition in situ.

Reference is made to the above-identified patent applications for a detailed description of the various polymers, their compositions, manufacture and general use. The disclosures of the above-identified Hubbell et al. applications are incorporated by reference, in their entireties, as part of the disclosure herein.

It is among the general objects of the present invention to provide devices and techniques for effectively and efficiently delivering and applying the liquid compositions (referred to as "prepolymers") to targeted tissue lumens, and then initiating the polymerization reaction in situ.

SUMMARY OF THE INVENTION

The invention includes devices for applying a polymeric material to a surface of a targeted tissue lumen or space, whether natural or induced, within a human or animal patient. The coating is applied as a prepolymer composition which then is irradiated with light, such as actinic light, to initiate and cause polymerization. In one embodiment, adapted for providing a "thick" gel to the interior surface of a lumen, the device comprises a catheter system having proximal and distal occlusion elements, such as radially expandable balloons, to define a treatment space, a molding member positioned between the occlusion elements to mold the prepolymer, and an optical emitter to provide a substantially uniform light field within the treatment space to uniformly polymerize the prepolymer.

In another embodiment, useful for providing a "thin" gel to the surface of a tissue lumen, the device comprises a catheter system having proximal and distal occlusion elements to define a treatment space, and an optical emitter to provide a substantially uniform light field within the treatment space. Unlike the device used for providing a thick gel, in the thin-gel embodiment, a molding member positioned between the occlusion elements is not used.

In still another embodiment, either of the devices described above can have a single occlusion element. In this embodiment, rather than defining the treatment space as that area between proximal and distal occlusion elements, the treatment site is defined as that region extending a short distance from the occlusion element in which light from the emitter, the prepolymer, and an optional photoinitiator, converge. Additionally, for certain applications, the occlusion elements can be eliminated entirely.

It is among the general objects of the invention to provide a device for efficiently and effectively applying polymerizable materials to tissue, including living tissue, and for initiating polymerization of the composition in situ.

A further object of the invention is to provide an apparatus for applying either a thin or thick film of a polymer on a targeted tissue lumen.

Another object of the invention is to provide devices of the type described that are suited particularly, although not exclusively, for use in percutaneous, transluminal surgical applications.

DESCRIPTION OF THE DRAWINGS

The foregoing and other objects and advantages of the invention will be appreciated more fully from the following further description thereof, with reference to the accompanying drawings wherein:

FIGS. 5A and 5B are schematic representations of still another embodiment of a device for providing a thick polymeric film on a luminal wall.

FIGS. 11A and 11B are schematic representations of a third embodiment of a device for providing a polymeric barrier layer on a luminal wall.

DESCRIPTION OF THE PREFERRED EMBODIMENTS

The following detailed description of the invention is made in the context of use as an adjunct to percutaneous transluminal surgical procedures. It should be understood, however, that the invention may be used in other surgical environments where it may be beneficial to apply and polymerize material directly on tissue.

The devices of the present invention are adapted to allow a physician to apply a polymeric paving material to the interior of body lumens or spaces, whether natural or induced. The devices may be configured in a manner that allows the physician to provide either a thick polymeric coating or a thin "interfacial" coating on the tissue surface. In the case of devices for providing a thick coating, the device can include at least one occlusion element to define at least one end of a treatment space, a molding member to mold and shape the coating material into a desired configuration, and an optical emitter for transmitting light to the coating material in order to initiate polymerization of the material. Likewise, in the case of devices for the application of thin "interfacial" polymers, the devices can include at least one occlusion element to define at least one end of the treatment space, and an optical emitter for transmitting light to the coating material. Although, as will be described below, numerous embodiments of molding members and occlusion elements are contemplated, for the sake of simplicity, each of the molding members and occlusion elements shown in the Figures comprise inflatable balloons unless otherwise noted.

Figure 1:
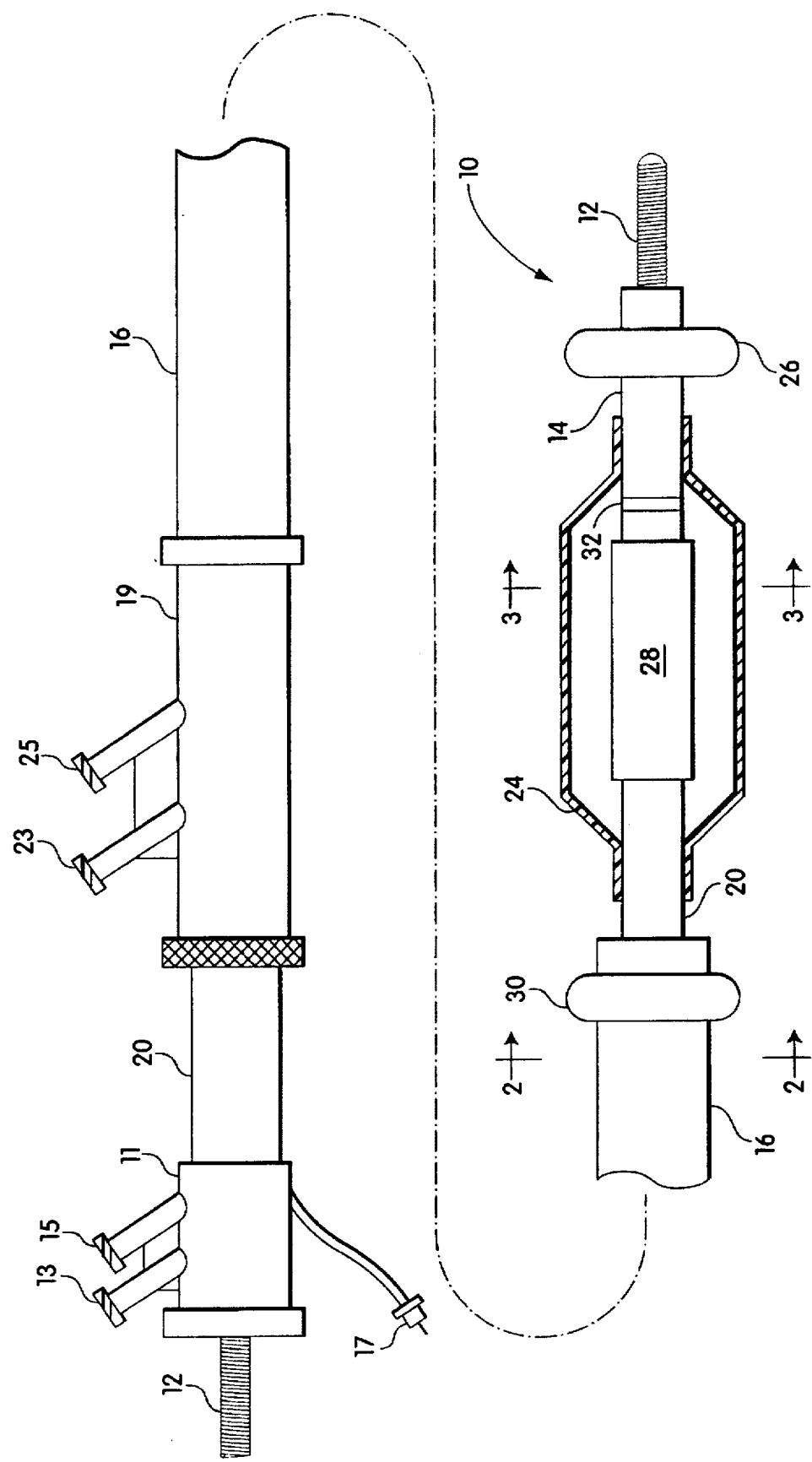
FIG. 1 is a schematic representation of one embodiment of a device for providing thick polymeric gels on the interior of a body lumen.

FIG. 1 is an illustration of one embodiment of a device for applying thick gels to tissue lumens. In the embodiment depicted in FIG. 1, the device 10 comprises three separate elements: a guidewire 12, a balloon catheter 14 and a sheath 16. The guidewire 12 may be any of a wide variety of guidewires known in the art for intraluminally guiding a catheter to a treatment site such as a coronary artery. The balloon catheter 14 comprises an elongated tubular shaft 20 having a central lumen, a molding member comprising molding balloon 24 and a distal occlusion element comprising distal occlusion balloon 26, both balloons being mounted near the distal end of the shaft 20. An optical emitter 28 is mounted within the interior of the molding balloon and serves to supply a substantially uniform field of light for carrying out the photopolymerization process in a manner described below. One or more radiopaque markers 32 comprising, for example, bands of a radiopaque metal such as tantalum, can optionally be positioned at various locations on the device. The sheath 16 includes two lumens. One is an annular space defined in part by the interior of the sheath, and is sufficiently large to surround the balloon catheter 14 when the molding balloon 24 and the distal occlusion balloon 26 are deflated. A second communicates with a proximal occlusion element which comprises a proximal occlusion balloon 30 mounted at or near the distal end of the sheath.

The proximal end of the device includes a hub assembly 11, having a central lumen to access the central lumen of the catheter shaft 20, a molding balloon inflation port 13, a distal occlusion balloon inflation port 15, and an optical fiber connector 17 which is attachable to a light source (not shown) to provide light to the optical emitter 28. An additional hub 19 is provided. Hub 19 is operatively connected to sheath 16 to serve as an actuator to position the sheath and the proximal occlusion balloon 30. Hub 19 also acts as a hemostatic valve. A collar 21 positioned at the proximal end of hub 19 allows the practitioner to position the sheath. Hub 19 includes a proximal occlusion balloon inflation port 23 and a treatment fluid injection port 25 through which fluids may be injected into the treatment space via an annular space (described below) between the interior of the sheath 16 and the exterior of the catheter shaft 20.

Figure 2:
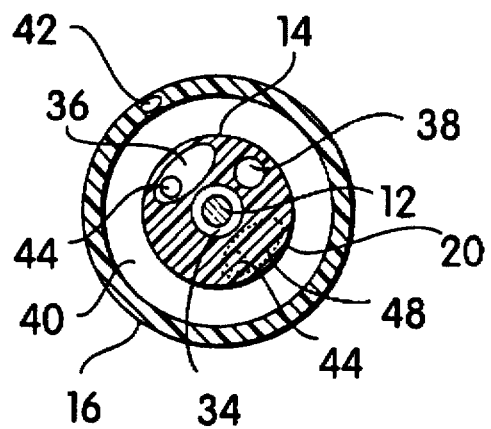
FIG. 2 is a cross-sectional view through line 2—2 of FIG. 1 at a region proximal to a proximal occlusion balloon.

As may be seen in FIG. 2, the shaft 20 of the balloon catheter 14 can include three lumens extending from its proximal end. A central lumen 34 provides a space through which the guidewire 12 may be passed. A molding balloon inflation lumen 36 communicates with the interior of the molding balloon 24 and molding balloon inflation port 13, thereby allowing the molding balloon to be inflated. Similarly, a distal occlusion balloon lumen 38 communicates with the interior of the distal occlusion balloon 26 and distal occlusion balloon inflation port 15, thereby allowing that balloon to be inflated.

In each embodiment described herein, the device need not be limited solely to catheters having a central lumen passing entirely though the catheter shaft. Rather, the catheters can include a separate, shorter lumen having one end which exits the catheter at or near the distal end of the catheter shaft and a second opening somewhat proximal to the distal end of the shaft. Such so-called "rapid exchange" or "monorail" catheters are designed to facilitate catheter exchanges while maintaining positioning of a guidewire. Monorail catheters are known in the art, being described, for example, in U.S. Pat. No. 4,762,129 to Bonzel.

As is also shown in FIG. 2, the sheath 16 surrounds the balloon catheter 14 and provides an annular space 40 through which fluids may be injected into a treatment space defined between the proximal 30 and distal 26 occlusion balloons. The sheath 16 includes a proximal occlusion balloon lumen 42 which communicates with the interior of the proximal occlusion balloon 30 and proximal occlusion balloon inflation port 23, and allows that balloon to be inflated.

Referring to FIG. 1, an optical emitter 28 is positioned within the interior of the molding balloon 24 and serves to direct light provided by at least one, and preferably a plurality of optical fibers 44 circumferentially outward in a substantially uniform manner. Referring again to FIG. 2, the optical fibers communicate with the emitter 28 either through the molding balloon inflation lumen 36, or, in the alternative, through a separate optical fiber lumen 48 (shown in phantom in FIG. 2) provided in the shaft 20.

Figure 3:
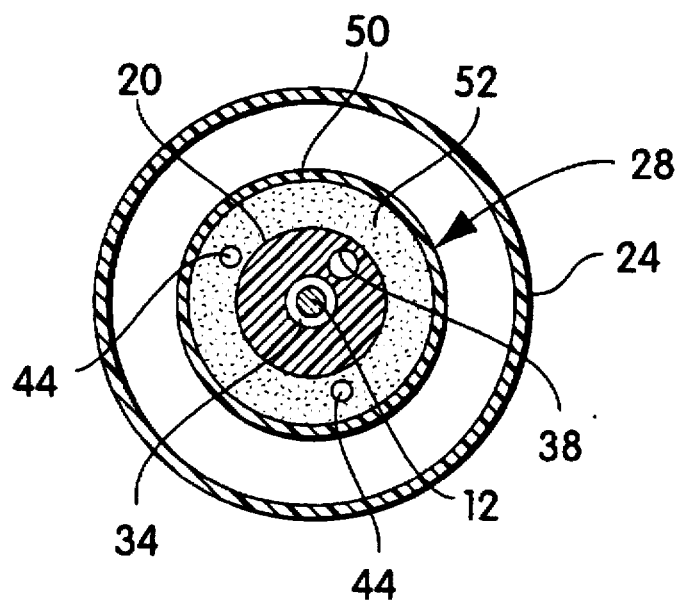
FIG. 3 is a cross-sectional view through line 3—3 of FIG. 1 at a region within a molding balloon.

In one embodiment, shown in FIG. 3, the optical emitter 28 comprises a flexible, translucent tube 50 containing a light scattering filler 52. The filler can comprise a translucent matrix containing a light-scattering medium such as titanium dioxide ($TiO_2$) particles. Other light scattering media suitable for use in accordance with the invention include $Zr_2O_3$, $Ba_2SO_4$, diamond dust, glass beads and combinations thereof, with or without $TiO_2$. The distal ends of the optical fibers 44 terminate within the light-scattering filler to allow light exiting from the fibers to be scattered in a substantially uniform radial and circumferential manner. In another embodiment, the catheter shaft 20 may be translucent at least at its distal end. A lumen passing through the translucent portion may be filled with a light-scattering filler as described above, and an optical fiber or fibers can be positioned within the filler. The optical fiber or fibers may be etched, cleaved, tapered or otherwise modified prior to insertion into the filler. The resulting catheter has, as an integral element, a light scattering optical emitter. The emitter may be attached to the optical fiber by taper joint, lap joint, or other known joining means.

A separate light source/controller (not shown) is connected to the proximal ends of the fibers via optical fiber connector 17 and serves to transmit light through the fibers into the emitter. By varying the concentration and composition of the scattering particles, and the number, positioning, and shape of the distal ends of the fibers, the intensity of the light field in the axial and circumferential directions can be controlled. Methods for achieving desired distributions of light intensity are known in the art and include simple arrays of scattering particles embedded in plastic as exemplified in U.S. Pat. No. 5,169,395 to Narciso, Jr.; and gradients of scattering particles as exemplified in U.S. Pat. No. 5,196,005 to Doiron et al.

The flexible, translucent tube 50 of the emitter 28 comprises a flexible material which minimizes absorption of light in a wavelength spectrum provided by the light source/controller. Numerous translucent polymeric materials including polyethylene terephthalate, polytetrafluoroethylene, polypropylene, silicone, and the like can be used. Polyethylene is preferred. The light scattering filler 52 preferably comprises a transparent or translucent matrix, for example an epoxy adhesive, containing the light-scattering particles. Like the emitter tube 50, the matrix containing the light-scattering particles must be substantially transparent to the wavelength spectrum of light which is to be passed through the emitter. Similarly, the molding balloon and the balloon inflation medium must be transparent to the light in order to allow the light to pass through the balloon and the medium and into the prepolymer material positioned in the treatment space between the proximal and distal occlusion balloons.

Figure 6:
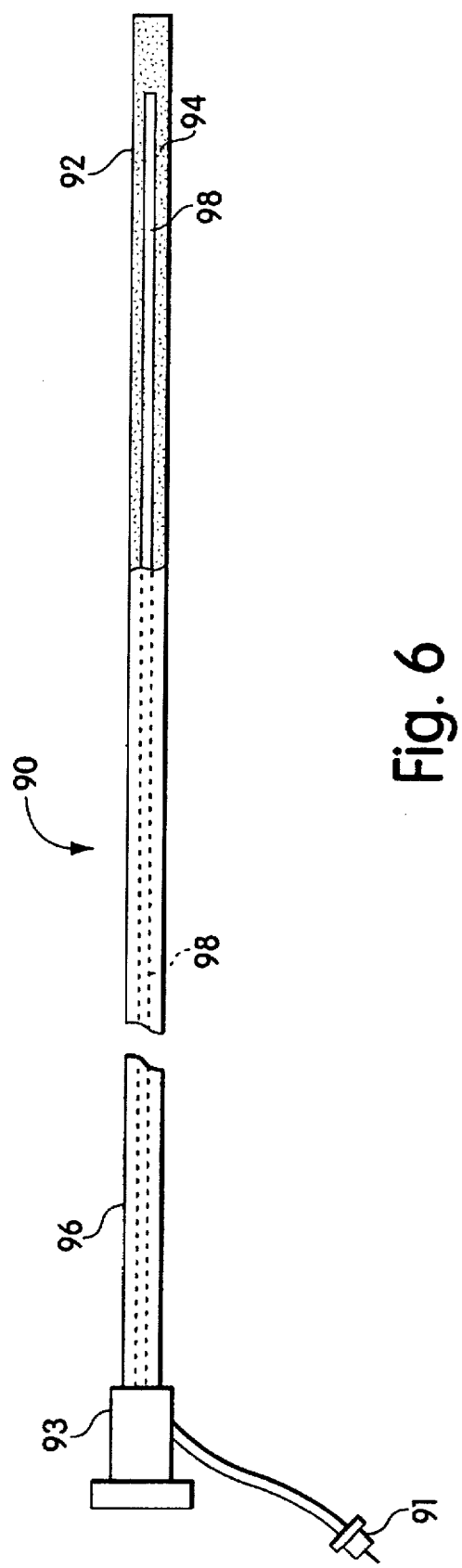
FIG. 6 is a schematic representation of an optical emitter catheter.

As an alternative, the emitter may be formed integrally on the distal end of the optical fibers themselves. For example, the distal end of the fibers may be chemically or mechanically modified in a manner which causes the fibers to radiate light laterally in the region of modification. Thus, in one embodiment, the distal end of the fibers may be ground or chemically modified to "frost" the fiber, thereby to provide light scattering sites directly on the fiber surface. Optical fibers modified in this manner can simplify the manufacture of the devices in that the need to assemble a separate optical emitter within the molding balloon portion of the device is eliminated. Still another emitter embodiment will be described below in connection with FIG. 6.

In one embodiment, the catheter shaft 20, at least in the region of the optical emitter 28, is transparent to light in the wavelength spectrum being used to prevent "shadowing" of the light. Alternatively, a reflective coating may be formed about the catheter shaft 20 in the region of the optical emitter to reflect any light scattered toward the shaft by the light scattering medium. For light in the visible spectrum, the reflective coating preferably comprises a thin coating of silver, and for light in the infrared spectrum, the reflective coating preferably comprises a thin coating of gold. Such coatings can be deposited using any of a variety of known methods for depositing metal on polymeric surfaces, including but not limited to sputtering, ion bombardment, and ion-assisted vapor deposition. It is noted that these modifications are not mandatory, however, as satisfactory results can still be achieved even if the shaft 20 in the region of the optical emitter 28 is not reflective of or translucent to the light. In that case, however, the catheter shaft must be such that it does not absorb light to the extent that it is heated to or above a temperature at which it will deform.

The catheter shaft 20 may be fabricated of any of a wide variety of materials that are sufficiently flexible and biocompatible. For example, polyethylenes, nylons, polyvinylchlorides, polyether block amides, polyurethanes, and other similar materials are all acceptable. It is preferred that the material have a low coefficient of friction, at least within the central lumen 34 to facilitate movement of the device over the guidewire 12. Alternatively, the central lumen 34 may be coated with a material to lower the frictional forces between the luminal walls and the guidewire. For example, if the catheter comprises a urethane, a polyethylene oxide-based material may be coated onto the lumens of the device to provide lubricity.

The molding balloon 24 comprises a non-compliant or moderately compliant balloon such as those typically used in angioplasty procedures. Materials such as polyethylene terephthalates or crosslinked polyethylenes exhibit little change in maximum diameter over a wide range of inflation pressures, and accordingly offer desirable properties. Irradiated polyethylenes are also desirable in that they have low surface energy, thereby minimizing the effect of polymeric materials sticking to the molding balloon. Since non-compliant balloons, when inflated, maintain a substantially constant size regardless of their internal pressure, it is preferred that in the case of thick gel applications the balloon be sized approximately 0.20-1.0 mm less than the diameter of the vessel to be treated, thereby providing a gel coating on the interior of the lumen having a thickness of approximately 0.10-0.50 mm. In the alternative, a moderately compliant balloon such as one made of a urethane, a polyolefin or a nylon may be used. With moderately compliant balloons, a single device can be used to cover a wider range of treatment vessel diameters while allowing a tailored gel thickness.

At least part of the molding balloon, and the medium used to inflate the balloon, must be transparent to the light provided by the optical emitter. The balloon may be entirely transparent, or only the flatter portion parallel to the vessel wall may be transparent, with the conical portions coated to block the exciting light. A suitable inflation medium comprises a mixture of saline and an iodinated contrast agent. The mixture is both transparent to light provided by the emitter and radiopaque to allow fluoroscopic visualization when the balloon is inflated. It is preferred that the balloon be relatively thin walled so that its deflated condition will offer a low profile to facilitate delivery of the device through the sheath.

The balloon must readily release and not stick to the material which is to be photopolymerized. Polyethylene and polyolefin balloons have low energy surfaces and are therefore desirable. Alternatively, a coating having low surface energy may be used to facilitate release of the polymeric material from other balloons. Such coatings include silicone oils, fluoropolymers, surfactants, hydrogels or other materials having low surface energy.

Although shaped differently, the distal occlusion balloon may be formed of a material similar to that of the molding balloon. However, it is preferred that the distal occlusion balloon be formed of a relatively compliant material to offer the physician greater flexibility in the inflated size of the balloon in order to provide complete occlusion of the body lumen at the site at which the distal occlusion balloon is positioned. Furthermore, compliant occlusion balloons are likely to be less traumatic to the tissue lumen, thereby reducing the potential for complications as a result of over-inflation. Suitable compliant balloon materials include, but are not limited to latex, urethanes, polyether block amides, and the like. The distal occlusion balloon need not be transparent to light provided by the optical emitter.

The occlusion sheath 16 comprises an elongate flexible tube having a wall thickness on the order of about 0.003-0.004 inches, and an internal diameter large enough to contain the balloon catheter 14 when both the molding balloon 24 and the distal occlusion balloon 26 are in their deflated states. The interior diameter of sheath 16 must be substantially larger than the outer diameter of the balloon catheter shaft 20 in the region proximal to that region of shaft 20 extending distally from sheath 16 when shaft 20 is in its operative position. In this way, an annular space 40 is defined between the sheath and the shaft 20 through which the photopolymerizable prepolymer and other fluids may be injected into the treatment site, and through which other devices may be inserted if desired. Additionally, the sheath is axially moveable relative to the shaft in order to allow the shaft and its balloons to be withdrawn through the sheath to provide interchangability of such devices. Furthermore, by allowing relative axial movement between the proximal and distal occlusion balloons, the axial length of the treatment space may be varied, thereby allowing the physician to tailor the device to the particular lesion being treated.

It is desirable that the interior wall of the sheath lumen have a low coefficient of friction to facilitate movement of the sheath over the balloon catheter. Among the materials that may be used to form the sheath are fluoropolymers, high density polyethylenes, polyether block amides, thermoplastic elastomers, or urethanes. As described above, in cases in which the lumen does not offer a sufficiently low coefficient of friction, coatings such as surfactants, hydrogels, silicone oils or fluoropolymers may be provided. The sheath further includes a proximal occlusion balloon lumen 42 which communicates with the interior of the proximal occlusion balloon 30 to allow that balloon to be inflated. The proximal occlusion balloon 30 is of substantially the same construction as that of the distal occlusion balloon 26 described above.

The outer diameter of each of the device components should be sized appropriately to facilitate delivery and to minimize profile. As such, the device can be inserted within a targeted lumen causing minimal trauma at the treatment site. In one embodiment, for delivery within the coronary vessels, the profile of the occlusion sheath is preferably no larger than about 1.6 mm (~0.065 inches) to allow delivery through a standard coronary guiding catheter. Likewise, the balloon catheter must be sized to move effectively within the sheath and to allow delivery of polymeric material in the space between the sheath inner diameter and the balloon catheter outer diameter. The device must also be sized to easily pass through obstructed lesions and to be deliverable over small diameter guidewires, such as guidewires having a diameter of approximately 0.30-0.45 mm (~0.012-0.018 inches) commonly used in the coronary arteries.

In one method of use, the device is positioned at a treatment site, typically post-angioplasty, using standard percutaneous transluminal catheterization procedures. Prior to insertion of the device into a patient, each of the proximal occlusion balloon, distal occlusion balloon, and molding balloon are deflated and the distal end of the sheath is advanced to a location proximal to the distal end of the balloon catheter. In a post-angioplasty procedure, the guidewire used to position the dilatation catheter is left in place. If the procedure is carried out at a time other than post-angioplasty, the guidewire is inserted into a patient and navigated until its distal end crosses a treatment location. Subsequently, the device is passed over the guidewire until the molding balloon has been positioned at the desired treatment location. Since the distal occlusion balloon is, in this case, mounted on the same shaft as the molding balloon, positioning of the molding balloon serves to position the distal occlusion balloon as well. The proximal occlusion balloon is then positioned proximal to the molding balloon to define the proximal end of the area to be treated. Once inflated in the manner described below, the region between the proximal occlusion balloon and the distal occlusion balloon defines a space that is referred to herein as the "treatment space".

Once the molding balloon is positioned at a desired treatment position and the proximal and distal occlusion balloons are positioned with desired spacing, the occlusion balloons are inflated to define the treatment space and to occlude the body lumen at both the proximal and distal ends of the treatment space. It is preferred that the proximal occlusion balloon be inflated prior to the distal occlusion balloon to allow blood and other biological fluids contained within the body lumen to be removed prior to sealing the treatment space between both occlusion balloons.

If desired, following inflation of the proximal occlusion balloon, the treatment space may be filled or flushed with a solution, such as an inert saline solution, to remove blood and other biological fluids from the treatment space prior to inflation of the distal occlusion balloon. The solutions may be introduced through a port such as a side arm on a Touhey-Borst adapter or a similar device positioned at or near the proximal end of the catheter shaft. In addition, or as an alternative, a non-inert solution such as a solution containing a pharmaceutical agent may be injected into the treatment space. Among the non-inert solutions, solutions of tPA, streptokinase, urokinase, and the like are preferred, although virtually any pharmaceutical or therapeutic agent capable of being applied using the devices disclosed herein and offering a desired pharmaceutical or therapeutic effect may be used, either alone or in various combinations. Additionally, it is contemplated that one or more therapeutic agents for treatment of tissue or for preventing the deposition of substances from body fluid contained in the vessel may be incorporated into a prepolymer solution.

As used herein, pharmaceutical or therapeutic agent refers to substances which alter the metabolism of cells or which reduce the tendency for thrombosis or morbidity within diseased portions of the tissue. Examples for use in coronary artery applications are vasodilating agents i.e., nitrates and calcium channel blocking drugs; anti-proliferative agents i.e., colchicine and alkylating agents; intercalating agents; growth modulating factors such as interleukins, transformation growth factor b, congeners of platelet derived growth factor and monoclonal antibodies directed against growth factors; anti-thrombotic agents, e.g., anti-GIIb/IIIa, trigramin, prostacyclin, salicylates, and tissue-factor pathway inhibitors; thrombolytic agents e.g., streptokinase, urokinase, tissue plasminogen activator (tPA) and anisoylated plasminogen-streptokinase activator complex (APSAC); anti-inflammatory agents, both steroidal and non-steroidal and other agents which may modulate vessel tone, function, arteriosclerosis, and the healing response to vessel or organ injury post intervention. Anti-proliferative drugs or high efficacy anti-inflammatory drugs are also useful for treatment of focal vasculitides or other inflammatory arteritidies, e.g., granulomatous arteritis, polyarteritis nodosa, temporal arteritis and Wegner's granulomatosis. Anti-inflammatory agents are also useful in connection with indications such as inflammatory bowel disease, Crohn's disease, ulcerative colitis and focal GI inflammatory diseases. In other applications, adhesives may be introduced in accordance with the invention to help heal dissections, flaps and aneurysms. Exemplary adhesives include cyanoacrylates, gelatin/resorcinal/formol, mussel adhesive protein and autologous fibrinogen adhesive. The term "therapeutic agents" does not encompass solubilizing or dissolving agents which disrupt the atherosclerotic plaque.

The flushing liquids may be injected into the treatment space through the annular space 40 between the sheath 16 and the balloon catheter shaft 20. Once the treatment space has been cleared of blood and other biological fluids, the distal occlusion balloon is inflated to thereby seal and define the treatment space.

As an alternative, the device may be provided with an additional flushing, or drain lumen whereby the flushing liquids injected into the treatment space exit through the additional lumen and out of the patient through the proximal end of that lumen. It is noted that since all liquids (i.e., flushing, prepolymer, photoinitiator) used in connection with the invention are biologically compatible, they need not be removed from the patient, but rather may be allowed to flow distally from the treatment site for later, natural biological removal.

The device may also be provided with a perfusion lumen that allows blood to bypass the treatment space during the treatment process. In particular, such a lumen includes one or more ports which communicate with the exterior of the catheter at a location proximal to the proximal occlusion element and distal to the distal occlusion element. During occlusion at one or both ends of the treatment space, blood can enter the perfusion lumen through the proximal perfusion port, travel within the perfusion lumen through the treatment space, and return to the blood vessel through the distal perfusion port. Thus, even if the occlusion elements are expanded for an extended period of time, some blood flow across the treatment space is provided, thereby providing blood to the lumen distal to the treatment space.

Following the optional flushing step, a prepolymer fluid to be photopolymerized is injected into the treatment space through the annular space 40. If an additional flushing lumen or a valve-occlusion balloon (described below) is not provided, it is preferred that the distal occlusion balloon be deflated simultaneously with injecting the prepolymer fluid into the treatment space. In this manner, the flushing fluid that occupies the treatment space prior to prepolymer injection will be displaced distally by the prepolymer. Once the prepolymer has replaced the flushing fluid in the treatment space, the distal occlusion balloon is inflated to contain the prepolymer. Alternatively, if a "flushing" lumen is provided, the flushing fluid can be displaced by the prepolymer and removed through that lumen. Although the prepolymer is described in detail in the aforementioned Hubbell applications, it is noted that it preferably contains a photoinitiator to cause crosslinking in the prepolymer upon exposure to light.

Once the prepolymer fluid has entered the treatment space, the molding balloon is inflated to thereby form the prepolymer fluid into an annular "sleeve" in contact with the interior surface of the body lumen. As noted above, the molding balloon is preferably expanded to a size which provides a clearance of between approximately 0.10 and 0.50 mm between the balloon surface and the interior surface of the body lumen. It is noted, however, that much greater clearance may be provided if thicker gels are desired. For example, the present invention could be used to provide gels having a thickness of 10 mm or greater if desired for a particular application. Thus, one primary function of the molding balloon is to provide a means for maintaining a patent lumen of predefined diameter following gel formation within the body lumen. As the molding balloon is inflated, excess prepolymer fluid will be forced back into the annular space 40 and the optional flushing lumen. Some fluid may also be forced past the occlusion elements, however, since the fluid is biocompatible, the excess fluid does not present a problem. Inflation of the balloon to the desired size can be monitored using fluoroscopy.

Upon expansion of the molding balloon, light energy is supplied through the optical fibers to the optical emitter. The light diffuses outwardly from the emitter, and through the balloon inflation medium and the balloon. Upon transmission through the balloon, the light energy is absorbed by the photoinitiator contained in the prepolymer fluid thereby causing the prepolymer to become crosslinked. Upon completion of the crosslinking procedure, the light source is turned off and the molding balloon is deflated, thereby leaving a polymeric sleeve having a thickness of approximately 0.10–0.50 mm on the interior surface of the body lumen. The proximal and distal occlusion balloons are then deflated and the device is withdrawn from the body lumen, leaving the sleeve in place.

It is noted that the specific sequence of the balloon inflation and light irradiation steps is intended merely as an example, and that many variations to the sequence are contemplated as well. For example, the molding balloon may be inflated simultaneously with introduction of light to the prepolymer material, or the photopolymerization process may be initiated prior to inflation of the molding balloon.

Additionally, as noted above, the device can be constructed to have only a single, proximal or distal occlusion balloon. In that case, rather than defining the treatment space by the sequential or simultaneous inflation of the proximal and distal occlusion balloons, the single occlusion balloon is inflated, the flushing liquid is injected, followed immediately by the injection of the prepolymer liquid. Upon injection of the prepolymer, photopolymerization is carried out as described above. In that case, the treatment space can be defined, in more general terms, as an area at which the polymer, light and tissue physically intersect at a given time.

Additionally, in some circumstances, it is possible to eliminate the occlusion balloons altogether. For example, if the polymeric material is to be applied to the surfaces of a natural or induced body lumen or space through which a body fluid is not continuously flowing, occlusion of the region to be treated can be eliminated if the body fluid can be adequately displaced by the injection of flushing solutions and/or the prepolymer liquid.

It is also noted that the elements of the device described above need not be separate. Rather, a single shaft incorporating any or all of the occlusion balloons, molding balloon, and optical emitter can be used to apply polymeric material to tissue surfaces using the methods described above.

Figure 4:
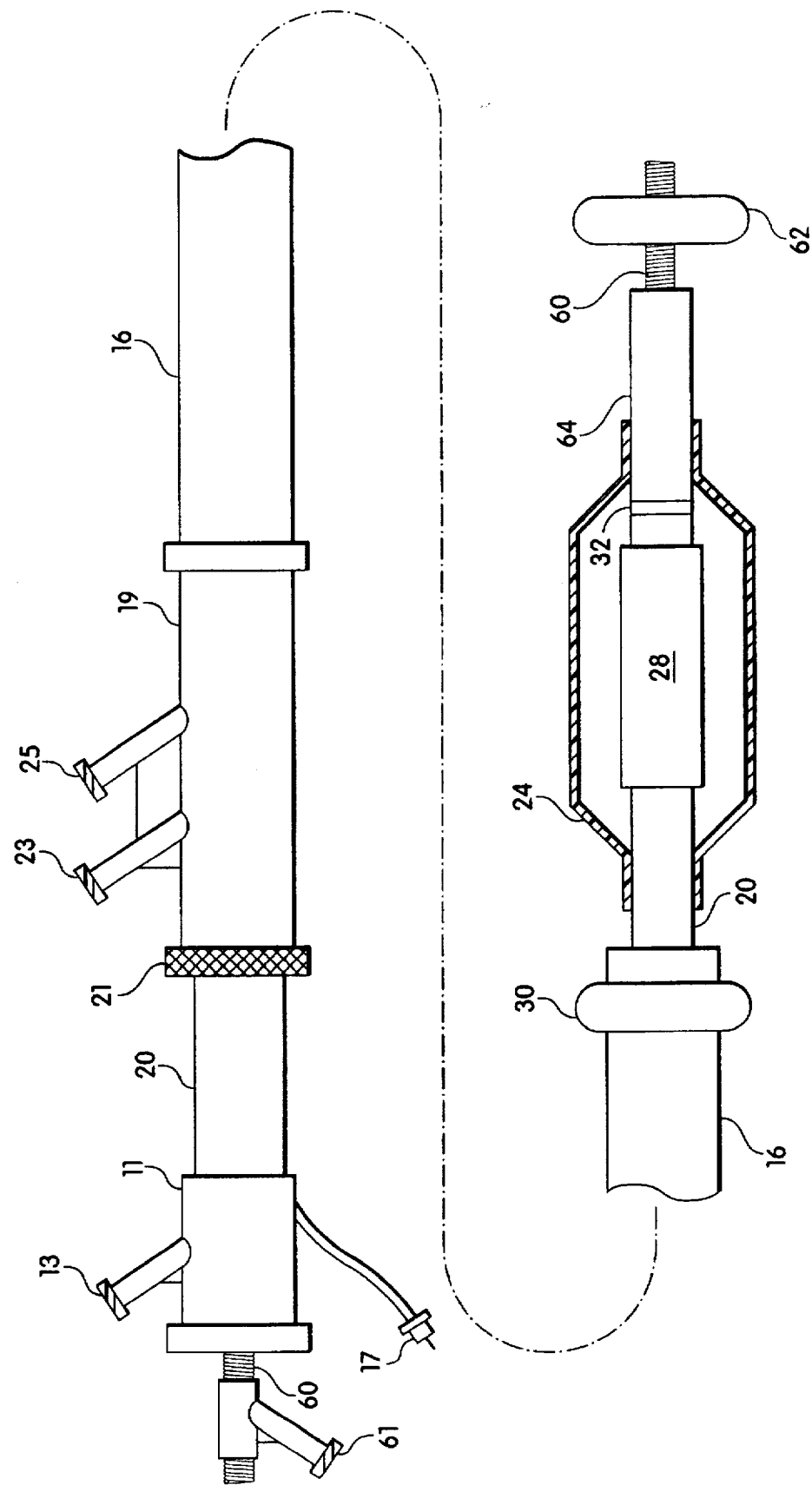
FIG. 4 is a schematic representation of a second embodiment of a device for providing thick polymeric gel on a luminal wall.

Another embodiment of the device is depicted schematically in FIG. 4. Although similar to the device of FIG. 1 in many aspects, the device of FIG. 4 differs in that the distal occlusion balloon is positioned on the guidewire, rather than on the balloon catheter shaft in the region distal to the molding balloon. Thus, the device comprises a guidewire 60 having a distal occlusion balloon 62 positioned at its distal end. Such so-called "balloon-on-a-wire" devices are known in the art, being described, for example in U.S. Pat. No. 4,582,181 to Samson and in U.S. Pat. No. 4,846,174 to Willard et al. The balloon catheter 64 is identical to that described previously with the exception that it does not include the distal occlusion balloon 62 or a lumen communicating with that balloon. In all other aspects, the molding balloon 24, the optical emitter 28, the sheath 16, the proximal occlusion balloon 30, and the marker 32 are identical to those described previously. Likewise, the proximal end of the device is similar to that of FIG. 1 with the exception that the distal occlusion balloon inflation port 61 has been positioned on the guidewire 60 consistent with the "balloon-on-a-wire" design.

Still another embodiment of the device is depicted schematically in FIGS. 5A and 5B. In that embodiment, the optical emitter is not included as part of the balloon catheter assembly, but rather, comprises a separate element that is inserted through the central lumen of the balloon catheter during the treatment procedure. More particularly, such a device 80 comprises three separate elements: a guidewire 12, a balloon catheter 82 and a sheath 16. As before, the guidewire 12 may be any of a variety of guidewires known in the art for intraluminally guiding a catheter to a treatment site. The balloon catheter 82 comprises an elongated tubular shaft 84 having a molding balloon 86 and a distal occlusion balloon 88, both mounted near the distal end of the shaft 84. One or more radiopaque markers 32 may be positioned on the balloon catheter shaft 84. The sheath 16 includes a lumen having a diameter sufficiently large to receive and enable passage of the balloon catheter 82 when the molding balloon 86 and the distal occlusion balloon 88 are deflated. A proximal occlusion balloon 30 is mounted at or near the distal end of the sheath.

The shaft 84 of the balloon catheter 82 includes at least three lumens: a first lumen communicating with the interior of the distal occlusion balloon 88, a second lumen communicating with the interior of the molding balloon 86 and a third lumen passing entirely through the shaft through which the guidewire 12 may be passed. The proximal end of the device is similar to that of FIG. 1 with the exception of the optical fiber connector 17 which is absent in the embodiment of FIG. 5A.

The device 80 further includes a separate optical emitter 90 that may be inserted through the balloon catheter shaft 84 after the guidewire 12 is removed. In one embodiment, depicted in FIG. 6, the optical emitter 90 has, at its distal end, a flexible, translucent tube 92 containing a light scattering filler 94, such as that described previously. The filler 94 is contained at the distal end of an elongated emitter shaft 96 having a central lumen therethrough. At least one optical fiber 98 passes through the lumen of the emitter shaft 26 and has its distal end terminating within the light scattering filler 94. The proximal end of the optical fiber 98 is connected to the light source/controller (not shown) via an optical fiber connector 91 which accesses the emitter shaft 96 through a proximal hub 93. One or more radiopaque markers may be provided on the emitter to assist in determining the position of the emitter once it is inserted into the patient.

The emitter tube 92 must be formed of a material that is substantially translucent or transparent to the light delivered through the optical fiber. Numerous translucent polymeric materials can be used, however, polyethylene is preferred. As an alternative, rather than mounting the emitter tube 92 on the distal end of the emitter shaft 96, the emitter tube and emitter shaft may be a single integral shaft formed of a translucent or transparent material and loaded with the light scattering filler only at its distal end. In another embodiment, a single optical fiber having a emitter positioned at its distal end may be used. In this embodiment, as before, the emitter comprises a transparent or translucent tube filled with a transparent or translucent binder material and a light scattering medium. The distal end of the optical fiber is inserted a short distance into the proximal end of the emitter, thereby providing a source of light to the emitter. As yet another alternative, the fiber can be inserted into an emitter formed of a translucent polymer having either inherent scattering characteristics or scattering media compounded therein. As still another alternative, at least one optical fiber having its distal end chemically or mechanically modified to radiate light laterally can be substituted for or combined with the emitters described above.

As with the other embodiments, in use, the device is positioned at a treatment site, typically post-angioplasty, using percutaneous transluminal catheterization procedures. Prior to insertion into a patient, the balloons of the device are deflated and the distal end of the sheath is advanced over the balloon catheter to a location proximal to the distal end of the catheter. The device is passed over the previously placed angioplasty guidewire until the molding balloon is positioned at the treatment location. The proximal occlusion balloon is then positioned at a desired proximal position. Once the molding balloon is positioned at a desired treatment position and the proximal and distal occlusion balloons are positioned with desired spacing, the occlusion balloons are inflated and the guidewire is withdrawn. As before, the balloons may be inflated either simultaneously or sequentially, the order being determined, in part, by the need to displace fluid in the treatment space prior to introduction of the prepolymer material. A flushing step, as described above, may optionally be performed.

After the guidewire has been withdrawn, the optical emitter 90 is inserted through the central lumen of the balloon catheter shaft 84 and advanced to position the emitter tube 92 in the portion of the shaft 84 surrounded by the molding balloon 86. A prepolymer material containing a dye or other photoinitiator is injected into the treatment space between the proximal 30 and distal 88 occlusion balloons and then molded and photopolymerized by expansion of the molding balloon 86 and illuminated with light from the optical emitter 90 in the manner described previously. Unlike the earlier embodiment, however, the balloon catheter shaft 84, at least in the region of the optical emitter tube 92, must be substantially transparent or translucent to light radiating from the emitter in order to allow that light to pass into and through the molding balloon. Upon completion of the crosslinking procedure, the light source is turned off and the molding balloon, the proximal occlusion balloon and the distal occlusion balloon are each deflated and the device is withdrawn from the body lumen, leaving a photopolymerized sleeve of polymeric material in place within the body lumen.

Each of the aforementioned embodiments is directed to a device for providing a relatively thick (i.e., about 0.10–0.50 mm) polymeric coating on the interior of a body vessel. In another embodiment, however, the device may be used to conduct an interfacial polymerization procedure to form a relatively thin (i.e., about 0.005–0.10 mm) barrier coating on the interior surface of a body lumen. Unlike the thick gel method described above in which the polymer contains a photoinitiator, the interfacial polymerization procedure involves, as a preliminary step, contacting the surface to be treated with a photoinitiator for a time sufficient to allow the tissue surface to adsorb a portion of the photoinitiator, and then contacting that surface with a polymer solution while simultaneously or subsequently irradiating the interface with light. The light interacts with the photoinitiator at the tissue surface causing a polymer film to crosslink and "grow" from the tissue surface into the lumen. After a brief period, the unpolymerized solution is removed from the treatment space leaving behind a thin barrier layer of crosslinked polymer on the luminal surface. Each of the thick gel and thin barrier layer processes are described in detail in the aforementioned, previously incorporated, Hubbell applications.

Figure 7:
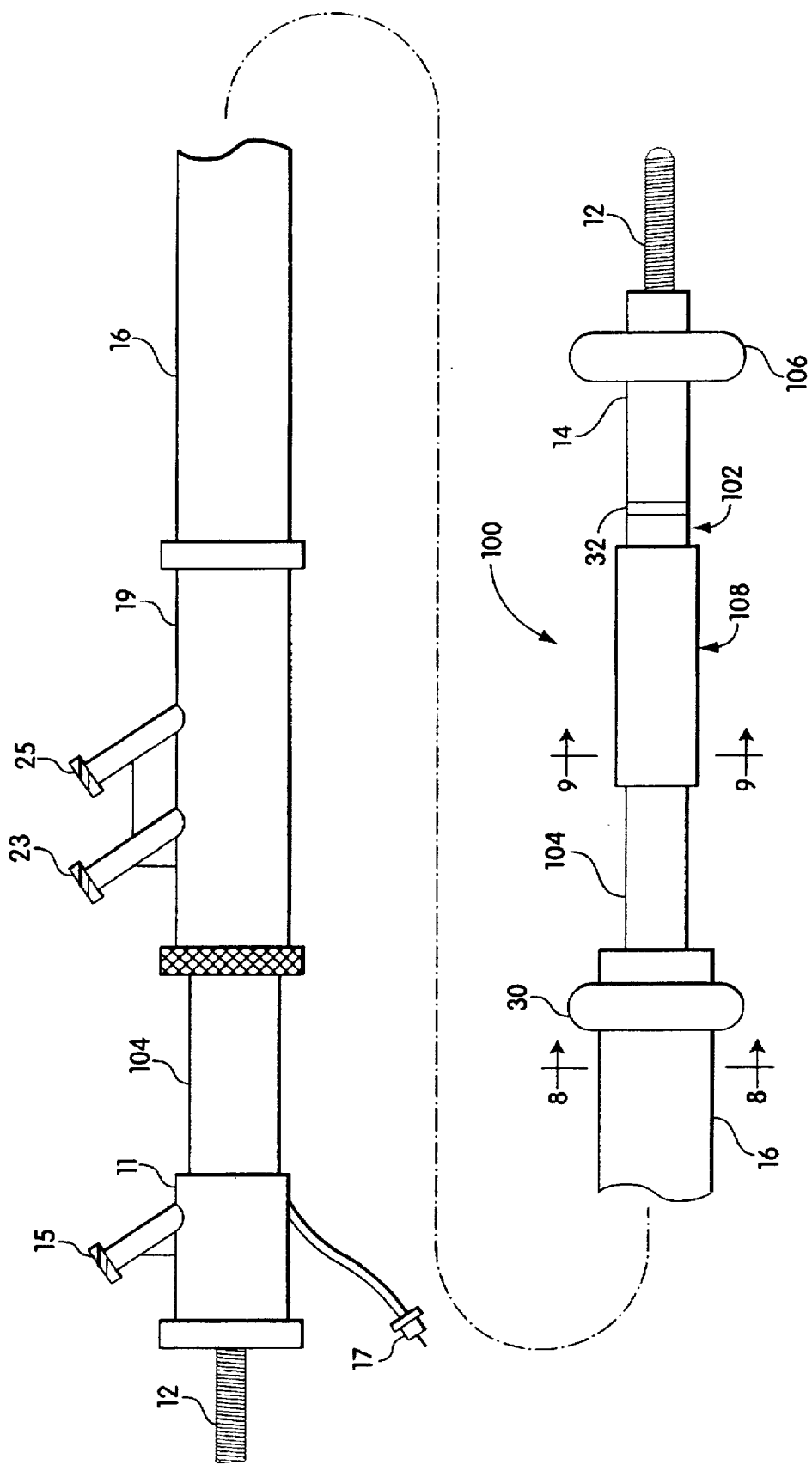
FIG. 7 is a schematic representation of one embodiment of a device for providing a polymeric barrier layer on a luminal wall.

The interfacial polymerization process can be carried out using a device such as that depicted schematically in FIG. 7. The device of FIG. 7 is substantially identical to that of FIG. 1 except that it does not include a molding balloon or molding balloon inflation lumen. Thus, the device 100 comprises three elements: a guidewire 12, a polymerization catheter 102 and a sheath 16. The guidewire is as described previously. The polymerization catheter 102 comprises an elongated tubular shaft 104 having a distal occlusion balloon 106 mounted near its distal end. An optical emitter 108 constructed in a manner substantially identical to that of the emitter in FIG. 1, is mounted on the polymerization catheter 102 in a region proximal to the distal occlusion balloon 106. One or more radiopaque markers 32 can optionally be positioned at various locations on the shaft 104. The sheath 16 includes a lumen having a diameter sufficiently large to enable passage of the polymerization catheter when the distal occlusion balloon 106 is deflated. A proximal occlusion balloon 30 is mounted at or near the distal end of the sheath.

Figure 8:
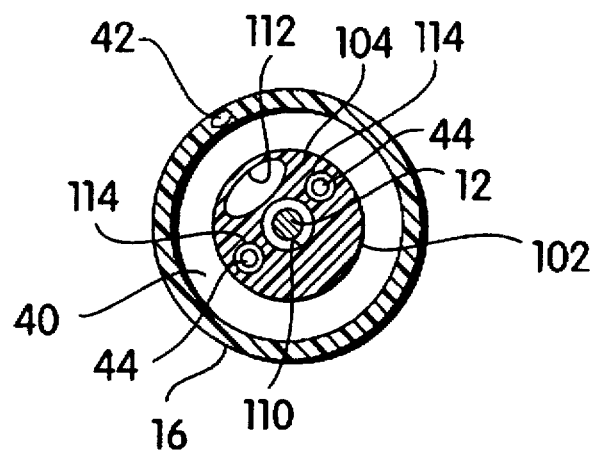
FIG. 8 is a cross-sectional view through line 8—8 of FIG. 7 at a location proximal to a proximal occlusion balloon.

As may be seen in FIG. 8, sheath 16 includes a proximal occlusion balloon lumen 42 which communicates with the interior of the proximal occlusion balloon 30 and allows it to be inflated. Shaft 104 of the polymerization catheter 102 includes multiple lumens extending from its proximal end. A central lumen 110 provides a space through which the guidewire 12 may be passed. A distal occlusion balloon lumen 112 communicates with the interior of the distal occlusion balloon 106, thereby allowing that balloon to be inflated. As also shown in FIG. 8, the sheath 16 surrounds the polymerization catheter 102 and provides an annular space 40 through which a prepolymer fluid may be injected into a treatment space positioned between the proximal 30 and distal 106 occlusion balloons. The catheter shaft 104 can further include at least one optical fiber lumen 114 through which at least one optical fiber 44 may pass, or in the alternative, the fiber may pass through the annular space 40 between the sheath and the polymerization catheter, or within the distal inflation lumen 112. In general, the optical fiber and emitter may be placed within any lumen. Moreover, it is not required that the guidewire or optical lumens be centered in the catheter shaft. The various lumens, in this and in other embodiments, may be arranged in any suitable pattern; for example, so as to maximize the size of the various lumens within a given catheter shaft size.

Figure 9:
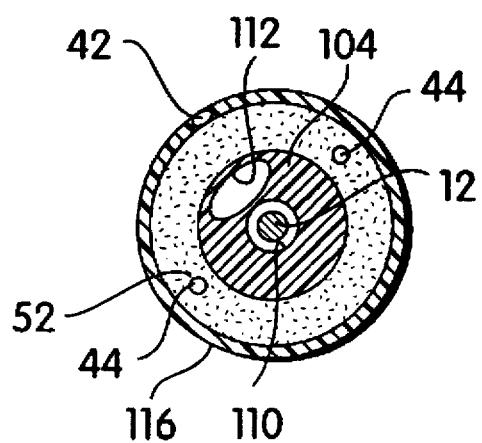
FIG. 9 is a cross-sectional view through line 9—9 of FIG. 7 across an optical emitter.

As shown in FIGS. 7 and 9, an optical emitter 108 positioned on the polymerization catheter shaft 104 comprises a flexible, translucent tube 116 containing a light scattering filler 52 of the type described earlier. One or more optical fibers 44 have distal ends terminating in the light scattering filler 52. As before, a reflective coating may be formed on the shaft 104 contained within the emitter 108. The material of construction for each of the occlusion balloons, the sheath, the polymerization catheter, and the optical emitter are as described above.

In use, the proximal and distal occlusion balloons are deflated and the sheath is extended over the polymerization catheter to a point proximal to the distal end of the polymerization catheter. The polymerization catheter with the distal occlusion balloon is guided over the guidewire to position the distal occlusion balloon at the distal end of the treatment site. The sheath is then positioned to place the proximal occlusion balloon at a desired proximal location. The proximal occlusion balloon is inflated to occlude the proximal end of the treatment site, and a flushing solution, as described previously, is injected through the annular space between the sheath and the polymerization catheter to flush blood and other biological fluids from the treatment site. Following flushing, a photoinitiator is injected through the annular space to coat and/or adsorb into tissue at the interior surface of the body lumen. Optionally, the unbound photoinitiator may be removed by flush. Then a prepolymer solution is injected into the treatment space between the proximal and distal occlusion balloons, which may displace the photoinitiator, and the distal occlusion balloon is inflated. As before, if the device is provided with a "flushing" lumen or a "valve-occlusion" balloon (described below), the distal occlusion balloon can be inflated earlier. In that case, fluid in the treatment space displaced by subsequent fluids would be displaced and removed through the "flushing" lumen. Once the prepolymer material fills the treatment space, light is directed through the optical fibers to the optical emitter and is caused to radiate therefrom in a substantially uniform radial, circumferential manner. Light which reaches the photoinitiator coating on the interior of the body lumen causes the prepolymer solution at the interface of the luminal wall to become photopolymerized, thereby forming a thin polymeric barrier layer on the luminal surface. The barrier layer "grows" outwardly into the lumen with continued illumination time. Unpolymerized material may then be flushed or aspirated from the treatment site. The balloons are then deflated and the device is withdrawn, leaving a thin barrier layer of polymeric material on the surface of the luminal wall. As used herein, the term "barrier layer" is meant to define, generally, a polymer layer that isolates a region of tissue. However, this term is meant to include also polymeric material which contacts tissue to provide structural support, to deliver pharmaceutical agents, and the like, where a continuous barrier is not necessarily formed.

Numerous variations such as those described in connection with the thick gel device are contemplated as well. For example, either one or both of the distal and proximal occlusion balloons may be eliminated and the various embodiments of the emitter may be substituted. Similarly, rather than having a multi-component device, each of the proximal and distal occlusion balloons, and the emitter, in their various combinations, may be mounted on a single multi-lumen shaft. In a preferred embodiment, at least one additional lumen is provided for introduction of a photoinitiator, a flushing solution, and/or prepolymer. If the single shaft embodiment is used, the ability to tailor the size of the treatment space is lost. However, the simplicity of the single shaft device overcomes the inability to vary the treatment space length for many applications. Likewise, the device may be used to withdraw flushing liquid in the manner described previously. Thus, it is intended that the numerous variations on the device described with respect to FIGS. 1–6 can be incorporated into the devices for application of thin interfacial gels as well.

Figure 10:
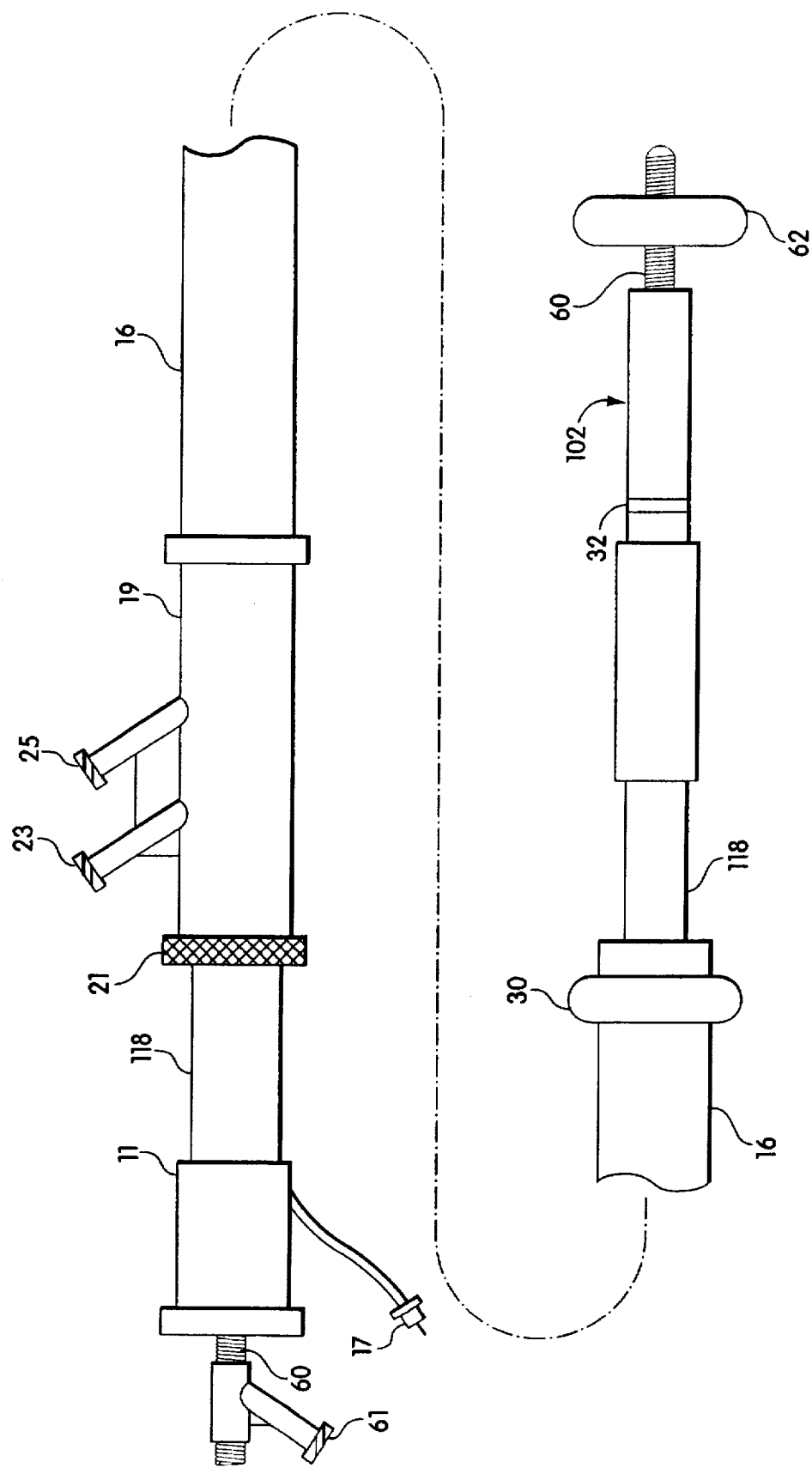
FIG. 10 is a schematic representation of a second embodiment of a device for providing a polymeric barrier layer on a luminal wall.

Another embodiment of the device is depicted schematically in FIG. 10. Although similar to the device of FIG. 7 in many aspects, the device of FIG. 10 differs in that the distal occlusion balloon is positioned on the guidewire rather than on the balloon catheter shaft in the region distal to the molding balloon. Thus, as in the thick gel embodiment, the device comprises a guidewire 60 having a distal occlusion balloon 62 mounted at its distal end. The polymerization catheter 118 is identical to that described previously with the exception that it does not include the distal occlusion balloon 62 or its related lumen. In all other aspects, the emitter 108, the sheath 16, the proximal occlusion balloon 30 and the marker 32 are identical to those described earlier. The proximal end of the device of FIG. 10 is similar to that of FIG. 4 with the exception that hub 11 does not include a molding balloon inflation port.

The method of operation of the device of FIG. 10 is substantially the same as that for the device depicted in FIG. 7. In particular, the proximal 30 and distal 62 occlusion balloons are deflated and the guidewire is navigated across a treatment site to position the distal occlusion balloon at the distal end of the treatment site. The polymerization catheter 118 is then advanced to position the emitter 108 at the treatment site. Subsequently, the sheath 16 is positioned to place the proximal occlusion balloon 30 at the proximal end of the treatment site. The proximal and distal occlusion balloons are then inflated, either simultaneously or sequentially in the same manner as described previously. The treatment site is then optionally flushed, coated with a photoinitiator, contacted with a prepolymer solution, and subjected to interfacial polymerization in the manner described above. Upon formation of the thin polymeric barrier layer on the luminal surface, the balloons are deflated and the device is withdrawn, leaving the polymeric barrier in place.

Still another embodiment of the present invention is depicted schematically FIGS. 11A and 11B. The device depicted in FIGS. 11A and 11B differs from the device of FIG. 7 in that a separate optical emitter 90 is used to provide light for the interfacial polymerization. Thus, the device of FIG. 11A includes a guidewire 12, a treatment catheter 120 having a distal occlusion balloon 106 at its distal end and a sheath 16 having a proximal occlusion balloon 30 positioned at or near its distal end. The treatment catheter 120 is transparent or translucent to the photopolymerizing light at least in the region that becomes exposed between the proximal and distal occlusion balloons. The proximal end of the device is similar to that of FIG. 7 with the exception of the optical fiber connector which is absent in the embodiment of FIG. 11A.

In use, typically post-angioplasty, the angioplasty guidewire is left in position across a treatment location. The proximal and distal occlusion balloons are deflated and the treatment catheter 120 is advanced distally to position the distal occlusion balloon at a location near the distal end of the treatment site. The sheath is then positioned over the guidewire to place the proximal occlusion balloon proximally adjacent to the treatment site. The proximal occlusion balloon is inflated and the treatment space is optionally flushed and coated with a photoinitiator in the manner described previously. The guidewire is withdrawn, and the optical emitter is then guided through the central lumen to position emitter tube 92 within the treatment space. A prepolymer solution is injected into the space between the proximal and distal occlusion balloons and the distal occlusion balloon is inflated. The prepolymer then is irradiated with light from the optical emitter in the manner described previously. The resulting polymerized layer comprises a thin barrier layer of polymeric material on the luminal surface.

The balloons are deflated and the device is withdrawn, thereby leaving the polymeric barrier in position on the luminal wall.

In each of the embodiments described herein, the treatment space is defined as that region between proximal and distal occlusion balloons which are inflated to isolate a segment of the vessel. It has also been noted that the proximal and distal occlusion balloons can each be of generally the same shape and material. In an alternative embodiment, applicable to each of the devices described above, one of the balloons, preferably the distal occlusion balloon, may be underinflated, fabricated of a particular material, or formed in a particular shape and/or size such that it is provided with a lesser ability to effectively occlude the lumen. Such a configuration offers certain advantages in that the resulting balloon can occlude the vessel while also allowing fluids injected into the treatment space to flow distally beyond the device. Balloons which offer the ability to occlude the lumen and allow some fluid to exit the treatment space during a fluid injection are referred to herein as "valve-occlusion" balloons. A valve-occlusion balloon can act, in part, as a one-way valve by allowing excess fluid delivered between the balloons to exit from the treatment space in a region that opens between the periphery of the balloon and the lumen wall during enhanced pressure conditions that occur when fluids are injected into the treatment space. As a result, fluid is allowed to flow beyond the treatment space, thereby alleviating the need for aspirating fluid proximally and limiting hydrostatic intramural chamber pressure without any retrograde flow or seepage of blood to the isolated segment.

Figure 12A:
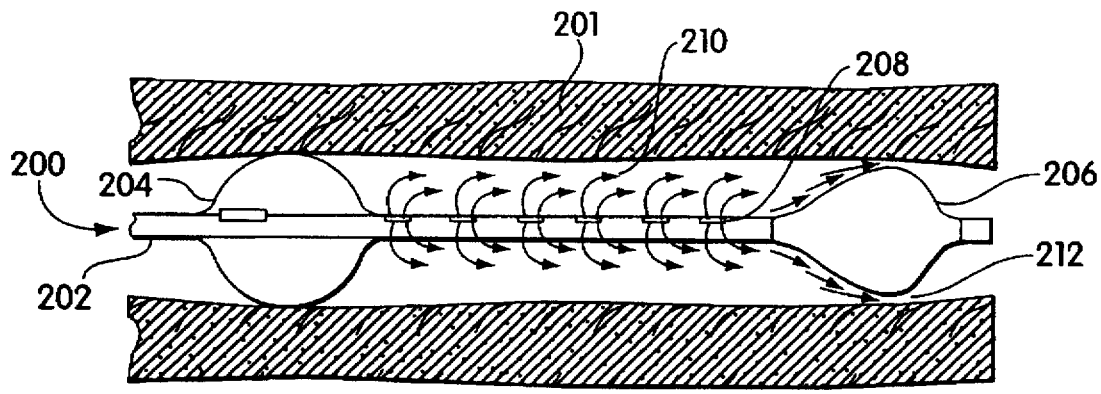
FIGS. 12A and 12B are schematic representations of a device having a valve-occlusion balloon.
Figure 12B:
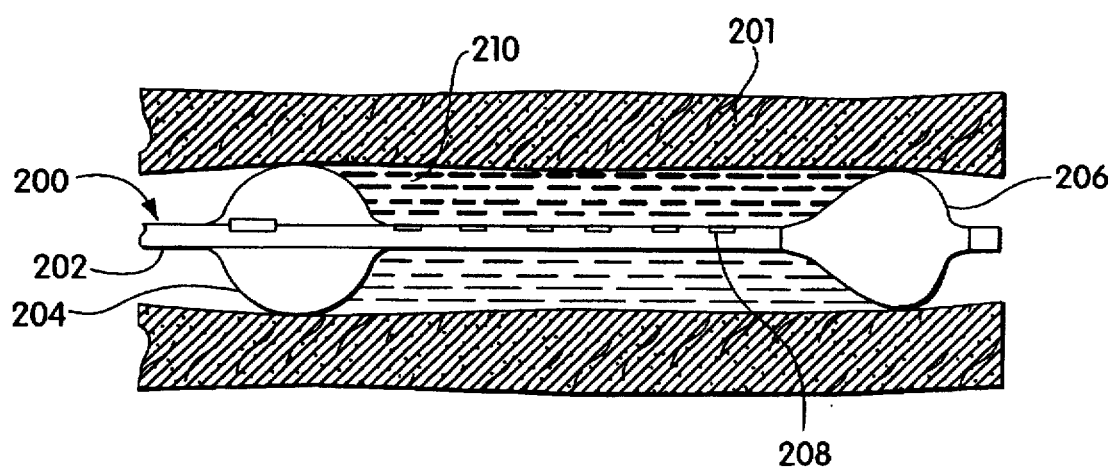

A catheter device including a valve-occlusion balloon is illustrated in FIGS. 12A and 12B. Referring first to FIG. 12A, the distal end of catheter device 200 is positioned within a blood vessel 201. The device comprises a catheter shaft 202 having proximal 204 and distal 206 occlusion balloons longitudinally spaced apart near the distal end of the catheter shaft 202. Unlike the devices described above, in which fluids are injected into the treatment space via an annular space formed between a sheath and a catheter, in the exemplary device of FIGS. 12A and 12B, the sheath has been eliminated and the proximal occlusion balloon 204 is mounted directly on the catheter shaft 202. Fluids 210 are injected into the treatment space through one or more ports 208 positioned on the catheter shaft between the occlusion balloons. The ports communicate with at least one lumen in the catheter shaft through which the fluids 210 can be injected. In this and other embodiments of the invention in which a port provides fluid communication between a lumen within a shaft and a region outside of the shaft, for example ports 208 providing fluid communication between a lumen within shaft 202 and the treatment space defined by occlusion balloons 204 and 206, the port or ports may be formed by shaving, or skiving, an exterior wall of the shaft to open the lumen.

As can be seen in FIG. 12A, a fluid 210 injected into the treatment space (and/or fluid in the treatment space displaced by fluid 210) is allowed to flow past the distal, valve-occlusion balloon 206 about the periphery 212 of that balloon when fluid pressure within the treatment space is sufficient. At the same time, the proximal balloon 204 occludes the proximal end of the treatment space and prevents fluid flow in the proximal direction. As shown in FIG. 12B, upon termination of injection of the fluid 210 into the treatment space, the distal occlusion balloon 206 reseals the distal end of the treatment space and contains the fluid injected therein.

Valve-occlusion balloon 206 can be formed in various ways. For example, it can be formed using a material that is more compliant than that from which occlusion balloon 204 is formed. Alternatively, both balloons may be manufactured of the same material, however valve-occlusion balloon 206 may be formed with a wall thickness that is less than that of occlusion balloon 204 to thereby render it more flexible. If the balloons are independently inflatable, valve-occlusion balloon 206 may be created by inflation to a lower pressure than that used to inflate occlusion balloon 204. A check valve or the like may be used to achieve underinflation of one balloon relative to the other. Alternatively still, valve-occlusion balloon 206 can have a shape that allows an increase in pressure in the treatment space between the balloons to facilitate removal of fluid from the treatment space past the valve-occlusion balloon. For example, valve-occlusion balloon 206 may be of a different shape and/or size relative to occlusion balloon 204 so that the area of contact between valve-occlusion balloon 206 and the interior wall of vessel 201 is smaller than the area of contact between balloon 204 and the interior wall of the vessel 201.

By eliminating the need for a separate drain lumen, the valve-occlusion balloon allows a catheter shaft of the same outer diameter to have a larger central, injection or guidewire lumen, or smaller catheter shaft, than would otherwise be possible. Likewise, if the device is intended to allow blood perfusion during the treatment procedure, the central lumen can be used for blood flow, thereby allowing a higher rate of flow through the catheter than would be possible if a separate drain lumen were required.

Figure 13A:
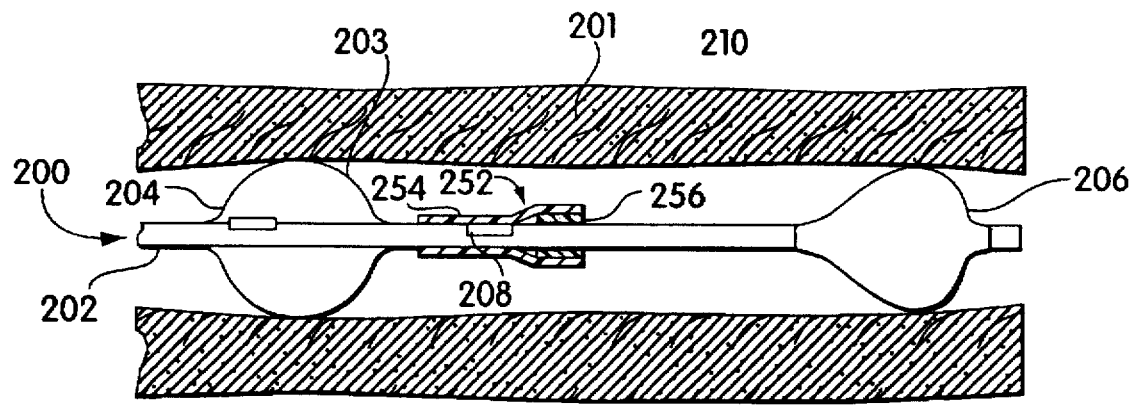
FIGS. 13A and 13B are schematic representations of a device having a flow-directing baffle.
Figure 13B:
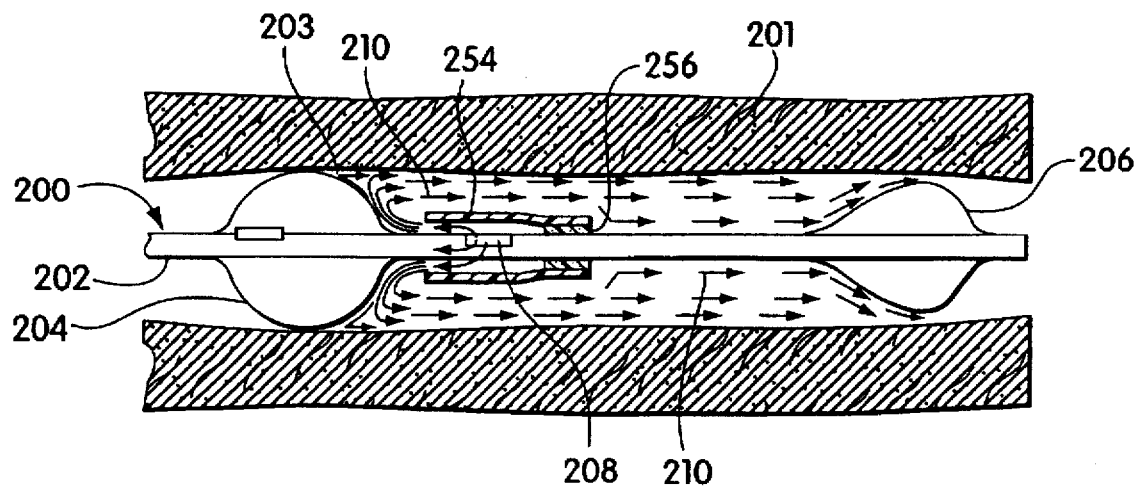

Infusion of a flushing fluid into a treatment space defined by two occluding balloons, as described above with reference to FIGS. 12A and 12B, following introduction of the photoinitiator or prepolymer may, in some circumstances, fail to completely flush the treatment space. With reference to FIG. 13A, this may result in unwanted residual material at the proximal end 203 of the treatment space adjacent proximal occlusion balloon 204. This effect can be eliminated by providing a baffle 252 on the catheter shaft 202 to direct fluid injected into the treatment space toward the proximal occlusion balloon 204 to thereby provide sufficient mixing and flushing at the proximal end of the treatment space. In this embodiment, baffle 252 comprises an elastic sheath 254 which surrounds the catheter shaft 202 in the region of an injection port 208 and is secured to the catheter shaft by an adhesive 256 at a location distal to the injection port 208. As is shown in FIG. 13B, fluid 210 exiting the injection port expands the elastic sheath 254 and is caused to flow proximally in the treatment space toward the proximal occlusion balloon 204. The proximal fluid flow removes residual material positioned at the proximal end 203 of the treatment space adjacent to the proximal occlusion balloon. Upon reaching the proximal end of the treatment space, the fluid begins a distal flow through the entire treatment space and ultimately flows beyond a distally-positioned valve-occlusion balloon 206. Fluid exiting from the injection port 208 is prevented from flowing immediately in the distal direction by the adhesive 256 which is used to secure the elastic sheath 254 to the shaft, effectively creating a barrier. Upon completion of the fluid injection, the elastic sheath 254 retracts about the injection port 208 and catheter shaft 202 into the configuration shown in FIG. 13A to prevent fluid in the treatment space from retrograde flow into the catheter shaft via the injection port. Thus, while acting as a baffle to direct injected fluid toward the proximal occlusion balloon, the elastic sheath also acts as a one-way check valve to prevent unwanted fluid flow back into the injection port.

In this and in other embodiments described herein in which fluid is caused to flow out of a port, the rate of fluid flow out of injection port 208 and into the treatment space between the occlusion balloons may be increased by blocking a lumen in shaft 202, through which the fluid passes, just distal to the port. For example, quick-setting adhesive or silicone may be injected into the lumen just distal to the port so that all fluid flow is directed into the treatment space.

In accordance with any of the embodiments described herein, if photoinitiator is rapidly adherent to the interior lumen tissue wall, then the interior surface may be prestained with photoinitiator before insertion of the device. For example, an artery may be flushed with normal saline, followed by photoinitiator dye in saline. Blood (or other local body fluid) then is allowed to flow while the device is being inserted and located at the treatment site. Although large areas of the vessel wall are stained with photoinitiator according to the method, only at the treatment site defined by the occlusion balloons are both prepolymer and light simultaneously present, thus localizing the creation of a barrier polymer layer.

As noted above, the molding and occlusion elements need not be limited to radially expandable balloons. Rather, occlusion can be achieved using other radially expandable structures. Alternatively, in a lumen having a decreasing diameter in the distal direction, distal occlusion may be achieved by advancing the distal tip of the device until it contacts the lumen walls in a region of decreased diameter.

In the embodiments above, the applied polymer layer has been presented as essentially annular. However, in some circumstances it may be desirable to make a layer which does not entirely cover the inner circumference of the vessel. For example, in any artery, it may be necessary to avoid a major side branch. Non-annular coatings can also be produced by catheters of the invention with minor modifications. For example, the molding balloon, when used, can be eccentric, so that prepolymer is not present on one side of the vessel. Alternatively, light can be prevented from passing through one or more sectors of the balloon or the catheter shaft, thereby preventing crosslinking of polymer in a particular zone. In order to properly position the non-coated zone, the catheter shaft should be provided with means for visualizing its radial orientation within the vessel or lumen. For example, a longitudinal strip of radio-opaque material—optionally also light-opaque—could be mounted on the catheter in the appropriate place.

Equivalents

Although specific features of the invention are included in some embodiments and drawings and not others, it should be noted that certain features may be combined with other features in accordance with the invention.

In addition, it should be noted that the invention is not intended to be limited to the specific materials and construction described herein.

It should be understood that the foregoing description of the invention is intended to be merely illustrative thereof, that the illustrative embodiments are presented by way of example only, and that other modifications, embodiments, and equivalents may be apparent to those skilled in the art without departing from its spirit.

Having thus described the invention, what we desire to claim and secure by Letters Patent is:

1. A method for providing a polymeric coating on a surface of a body lumen which comprises the steps of:

a) providing a device which comprises:
  i) an elongated shaft including at least one occlusion element for occluding the body lumen and an injection lumen for injecting a fluent prepolymer material into a space defined at least at one end by the occlusion element; and
  ii) an optical emitter positioned in the space defined at least at one end by the occlusion element;
b) positioning said at least one occlusion element at a desired location in the body lumen;
c) positioning the optical emitter at a treatment site;
d) actuating said at least one occlusion element to define a treatment space;
e) injecting a fluent prepolymer into the treatment space;
f) directing light through the optical emitter into the prepolymer to photopolymerize at least a portion of the prepolymer;
g) deactuating said at least one occlusion element; and,
h) withdrawing the device from the body lumen, thereby leaving a layer of polymeric material on at least a surface of the body lumen.

2. The method of claim 1 wherein at least one occlusion element comprises an inflatable balloon.

3. The method of claim 1 wherein the treatment space is flushed with at least one fluid prior to injecting the fluent prepolymer into the treatment space.

4. The method of claim 1 wherein the device further includes a molding member positioned in the treatment space, and the method further includes the step of using the molding member to form the fluent prepolymer solution into an annular or partially annular layer on the body lumen.

5. The method of claim 4 wherein the molding member comprises an inflatable balloon.

6. The method of claim 1 wherein at least one occlusion element comprises a valve-occlusion balloon.

7. A method for providing a polymeric coating on a surface of a body lumen which comprises the steps of:
a) providing a device which comprises:
  I) an elongated shaft including at least one occlusion element for occluding the body lumen and an injection lumen for injecting a fluent prepolymer material into a space defined at least at one end by the occlusion element; and
  ii) an optical emitter positioned in the space defined at least at one end by the occlusion element;
b) positioning said at least one occlusion element at a desired location in the body lumen;
c) positioning the optical emitter at a treatment site;
d) actuating said at least one occlusion element to define a treatment space and flushing the treatment space with a photoinitiator;
e) then injecting a fluent prepolymer into the treatment space;
f) directing light through the optical emitter into the prepolymer to photopolymerize at least a portion of prepolymer;
g) deactuating said at least one occlusion element; and,
h) withdrawing the device from the body lumen, thereby leaving a layer of polymeric material on at least a surface of the body lumen.

8. The method of claim 7, further comprising removing from the treatment space one of either photoinitiator that is not adsorbed by the body lumen surface or prepolymer that is not polymerized by the light prior to deactuating the at least one occlusion element.

9. The method of claim 7, wherein at least one occlusion element comprises an inflatable balloon.

10. The method of claim 7, wherein the device further includes a molding member positioned in the treatment space, and the method further includes the step of using the molding member to form the fluent prepolymer solution into an annular or partially annular layer on the body lumen.

11. A method for providing a polymeric coating on a surface of a body lumen which comprises the steps of:
a) providing a device which comprises:
  i) proximal and distal radially expandable occlusion elements, each being independently actuable and axially movable relative to the other and an injection lumen for injecting a fluent prepolymer material into a space defined between the proximal and distal occlusion elements; and
  ii) an optical emitter positioned at least partially between the proximal and distal occlusion elements, the emitter being axially movable relative to at least one of the occlusion elements;
b) positioning the proximal and distal occlusion elements at a desired location in the body lumen;
c) positioning the optical emitter at a treatment site;
d) actuating at least one of the proximal and distal occlusion elements to define a treatment space;
e) injecting a fluent prepolymer into the treatment space;
f) directing light through the optical emitter into the prepolymer to photopolymerize at least a portion of the prepolymer;
g) deactuating said at least one occlusion element; and,
h) withdrawing the device from the body lumen, thereby leaving a layer of polymeric material on at least a surface of the body lumen.

12. The method of claim 11 wherein at least one of the occlusion elements comprises an inflatable balloon.

13. The method of claim 11 wherein the treatment space is flushed with at least one fluid prior to injecting the fluent prepolymer into the treatment space.

14. The method of claim 11 wherein at least one occlusion element comprises a valve-occlusion balloon.

15. The method of claim 11 wherein the device further includes a molding member positioned in the treatment space, and the method further includes the step of using the molding member to form the fluent prepolymer solution into an annular layer on the body lumen.

16. The method of claim 15 wherein the molding member comprises an inflatable balloon.

17. A method for providing a polymeric coating on a surface of a body lumen which comprises the steps of:
a) providing a device which comprises:
  I) proximal and distal radially expandable occlusion elements, each being independently actuable and axially movable relative to the other and an injection lumen for injecting a fluent prepolymer material into a space defined between the proximal and distal occlusion elements; and
  ii) an optical emitter positioned at least partially between the proximal and distal occlusion elements, the emitter being axially movable relative to at least one of the occlusion elements;
b) positioning the proximal and distal occlusion elements at a desired location in the body lumen;
c) positioning the optical emitter at a treatment site;
d) actuating at least one of the proximal and distal occlusion elements to define a treatment space and flushing the treatment space with a photoinitiator;

e) then injecting a fluent prepolymer into the treatment space;

f) directing light through the optical emitter into the prepolymer to photopolymerize at least a portion of the prepolymer;

g) deactuating said at least one occlusion element; and, h) withdrawing the device from the body lumen, thereby leaving a layer of polymeric material on at least a surface of the body lumen.

18. The method of claim 17, further comprising removing from the treatment space one of either photoinitiator that is not absorbed by the body lumen surface or prepolymer that is not polymerized by the light prior to deactuating the at least one occlusion element.

19. The method fo claim 17, wherein at least one of the occlusion elements comprises an inflatable balloon.

20. The method of claim 17, wherein the device further includes a molding member positioned in the treatment space, and the method further includes the step of using the molding member to form the fluent prepolymer solution into an annular layer on the body lumen.

21. The method of claim 20, wherein the molding member comprises an inflatable balloon.

22. A method for providing a polymeric coating on a surface of a body lumen which comprises the steps of;

a) providing a device which comprises:
   i) an elongate tubular sheath having a proximal occlusion element near its distal end;
   ii) an elongate shaft, axially movable relative to the tubular sheath having a distal occlusion element near its distal end; and
   iii) an optical emitter positioned at least in part between the proximal and distal occlusion elements, the emitter axially movable relative to at least the proximal occlusion element;

b) advancing the elongate member such that the distal occlusion element is positioned at a desired location;

c) advancing the tubular sheath relative to the elongate member such that the distal end of the tubular sheath is positioned proximal to the distal end of the elongate member;

d) positioning the optical emitter at a treatment site;

e) actuating at least one of the proximal and distal occlusion elements to define a treatment space;

f) injecting a fluent prepolymer into the treatment space;

g) directing light through the optical emitter into the prepolymer to photopolymerize at least a portion of the prepolymer; and h) deactuating said at least one occlusion element; and, i) withdrawing the device from the body lumen, thereby leaving a layer of polymeric material on at least a surface of the body lumen.

23. The method of claim 22 wherein at least one of the occlusion elements comprises an inflatable balloon.

24. The method of claim 22 wherein the treatment space is flushed with at least one fluid prior to injecting the fluent prepolymer into the treatment space.

25. The method of claim 22 wherein the relative distance between the proximal occlusion element and the distal occlusion element is adjustable.

26. The method of claim 22 wherein at least one occlusion element comprises a valve-occlusion balloon.

27. The method of claim 22, wherein said elongate shaft is coaxial with said sheath for at least a portion of its length.

28. The method of claim 22 wherein the device further includes a molding member positioned at least in part in the treatment space, and the method further includes the step of using the molding member to form the fluent prepolymer solution into an annular layer on the body lumen.

29. The method of claim 28 wherein the molding member comprises an inflatable balloon.

30. A method for providing a polymeric coating on a surface of a body lumen which comprises the steps of:

a) providing a device which comprises:
   I) an elongate tubular sheath having a proxtmal occlusion element near its distal end;
   ii) an elongate shaft, axially movable relative to the tubular sheath having a distal occlusion element near its distal end; and
   iii) an optical emitter positioned at least in part between the proximal and distal occlusion elements, the emitter axially movable relative to at least the proximal occlusion element;

b) advancing the elongate member such that the distal occlusion element is positioned at a desired location;

c) advancing the tubular sheath relative to the elongate member such that the distal end of the tubular sheath is positioned proximal to the distal end of the elongate member;

d) positioning the optical emitter at a treatment site;

c) advancing the tubular sheath relative to the elongate member such that the distal end of the tubular sheath is positioned proximal to the distal end of the elongate member;

d) positioning the optical emitter at a treatment site;

e) actuating at least one of the proximal and distal occlusion elements to define a treatment space and flushing the treatment space with a photoinitiator;

f) then injecting a fluent prepolymer into the treatment space;

g) directing light through the optical emitter into the prepolymer to photopolymerize at least a portion of the prepolymer;

h) deactuating said at least one occlusion element; and,

I) withdrawing the device from the body lumen, thereby leaving a layer of polymeric material on at least a surface of the body lumen.

31. The method of claim 30, further comprising removing from the treatment space one of either photoinitiator that is not adsorbed by the body lumen surface or prepolymer that is not polymerized by the light prior to deactuating the at least one occlusion element.

32. The method of claim 30, wherein at least one of the occlusion elements comprises an inflatable balloon.

33. The method of claim 30, wherein the relative distance between the proximal occlusion element and the distal occlusion element is adjustable.

34. The method of claim 30, wherein the device further includes a molding member positioned at least in part in the treatment space, and the method further includes the step of using the molding member to form the fluent prepolymer solution into an annular layer on the body lumen.

35. The method of claim 34, wherein the molding member comprises an inflatable balloon.

36. A method for providing a polymeric coating on a surface of a body lumen which comprises the steps of:

a) providing a device which comprises:
  i) an elongated shaft including at least one injection lumen for injecting a flushing liquid, a photoinitiator, and a fluent prepolymer material into the body lumen; and
  ii) an optical emitter positioned adjacent to the surface to be coated;
b) guiding the device through a body lumen to position the optical emitter adjacent to the surface to be coated;
c) optionally injecting a flushing liquid into the lumen at the surface to be coated;
d) injecting a photoinitiator to stain the surface to be coated;
e) injecting a fluent prepolymer to contact surfaces stained with the photoinitiator;
f) directing light through the optical emitter into the prepolymer to photopolymerize at least a portion of the prepolymer and render it non-fluent; and
g) withdrawing the device from the body lumen, thereby leaving a layer of polymeric material on at least a surface of the body lumen.

37. A method as in claim 36 which further includes the step of injecting a flushing liquid into the lumen at the surface to be coated subsequent to the step of injecting the photoinitiator.

* * * * *

UNITED STATES PATENT AND TRADEMARK OFFICE
CERTIFICATE OF CORRECTION

PATENT NO. : 5,665,063
DATED : September 9, 1997
INVENTOR(S) : Laurence A. Roth et al.

It is certified that error appears in the above-identified patent and that said Letters Patent is hereby corrected as shown below:

In claim 18, line 12, please change "absorbed" to --adsorbed--.

In claim 19, line 15, please change "fo" to --of--.

In claim 22, line 25, please change "steps of;" to --steps of:--.

In claim 30, line 10, please change "proxtmal" to --proximal--.

Signed and Sealed this

Twenty-third Day of December, 1997

Attest:

BRUCE LEHMAN

Attesting Officer

Commissioner of Patents and Trademarks